(12) United States Patent
Ghosh et al.

(10) Patent No.: US 9,278,052 B2
(45) Date of Patent: Mar. 8, 2016

(54) METHOD FOR PRODUCING MONOLITHIC TABLETS

(75) Inventors: Soumojeet Ghosh, Gurnee, IL (US);
Didier Lefebvre, Mundelein, IL (US);
Bryan Wiesner, Lake Forest, IL (US);
Kevin Novak, Park Ridge, IL (US);
Thomas Kessler, Schifferstadt (DE)

(73) Assignees: AbbVie Inc., North Chicago, IL (US);
AbbVie Deutschland GmbH & Co. KG, Wiesbaden (DE)

( * ) Notice: Subject to any disclaimer, the term of this patent is extended or adjusted under 35 U.S.C. 154(b) by 472 days.

(21) Appl. No.: 13/289,990

(22) Filed: Nov. 4, 2011

(65) Prior Publication Data

US 2012/0205830 A1 Aug. 16, 2012

Related U.S. Application Data

(60) Provisional application No. 61/410,344, filed on Nov. 4, 2010.

(51) Int. Cl.
*B29C 43/02* (2006.01)
*A61J 3/06* (2006.01)
*A61J 3/10* (2006.01)

(52) U.S. Cl.
CPC ...... *A61J 3/06* (2013.01); *A61J 3/10* (2013.01)

(58) Field of Classification Search
CPC ................................ B29C 43/26; B29C 43/38
USPC .............................................. 264/40.4, 297.1
See application file for complete search history.

(56) References Cited

U.S. PATENT DOCUMENTS

| 4,601,768 | A | * | 7/1986 | Bouyoucos et al. | 156/73.5 |
| 5,840,224 | A | * | 11/1998 | Thary | 264/46.4 |
| 6,488,963 | B1 | | 12/2002 | McGinity et al. | |
| 6,884,379 | B1 | * | 4/2005 | Duqueine | 264/258 |
| 2005/0031546 | A1 | | 2/2005 | Bartholomaus et al. | |
| 2008/0311205 | A1 | | 12/2008 | Habib et al. | |
| 2010/0151028 | A1 | | 6/2010 | Ashworth et al. | |
| 2011/0217422 | A1 | * | 9/2011 | Suttle et al. | 426/89 |

FOREIGN PATENT DOCUMENTS

| DE | 19841244 | * | 7/2001 | A61J 3/06 |
| EP | 0358105 A2 | | 3/1990 | |
| JP | H08-099315 | * | 4/1996 | B29B 9/16 |
| WO | WO2005079760 A1 | | 9/2005 | |
| WO | WO2007085024 A2 | | 7/2007 | |

(Continued)

OTHER PUBLICATIONS

Byrn S.R., Solid State Chemistry of Drugs, Academic Press, 1982, Table of Contents.

(Continued)

*Primary Examiner* — James Sanders
*Assistant Examiner* — Kimberly A Stewart
(74) *Attorney, Agent, or Firm* — Lisa V. Mueller; Michael Best & Friedrich LLP

(57) ABSTRACT

The present invention relates to a process for producing monolithic tablets. The method employs a melt-processed composition containing at least on active agent and at least one thermoplastic binder. The invention further relates to a method for cutting and deflashing a belt of pre-shaped bodies of a melt-processed composition, wherein the pre-shaped bodies are interconnected by flash.

4 Claims, 3 Drawing Sheets

(56) References Cited

FOREIGN PATENT DOCUMENTS

| WO | 2009134848 A1 | 11/2009 |
| WO | WO2010140007 A2 | 12/2010 |

OTHER PUBLICATIONS

Ferry J.D., Viscoelastic Properties of Polymers, 3rd Edition, 1980, Table of Contents.

Harris J.M., Poly (Ethylene Glycol) Chemistry, Biotechnical and Biomedical Applications, Plenum Press, 1992, Table of Contents.

Remington, The Science and Practice of Pharmacy, 21st Edition, Troy D.B., et al., eds., Lippincott Williams & Wilkins, 2005, Table of Contents.

International Search Report and Written Opinion from PCT/US2011/059456 dated Mar. 5, 2012.

International Search Report for Application No. PCT/US2011/059458, mailed on Feb. 20, 2012, 3 pages.

Kuleznev V.N., and Gusev V.K., Plastics Processing Technology Basics, MIR Publishers, 2006, 14 pages.

Written Opinion for Application No. PCT/US2011/059458, mailed on May 4, 2013, 6 pages.

* cited by examiner

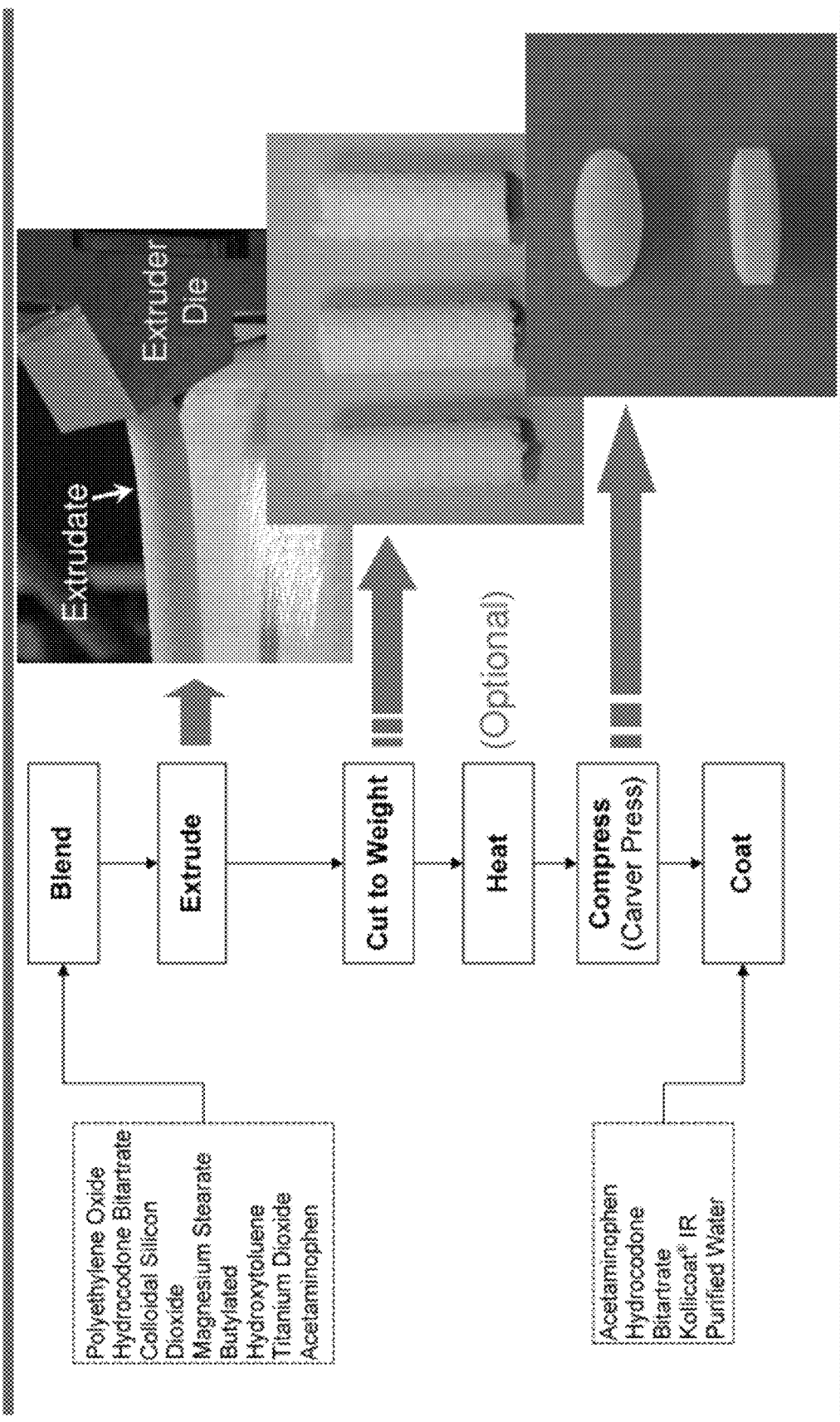

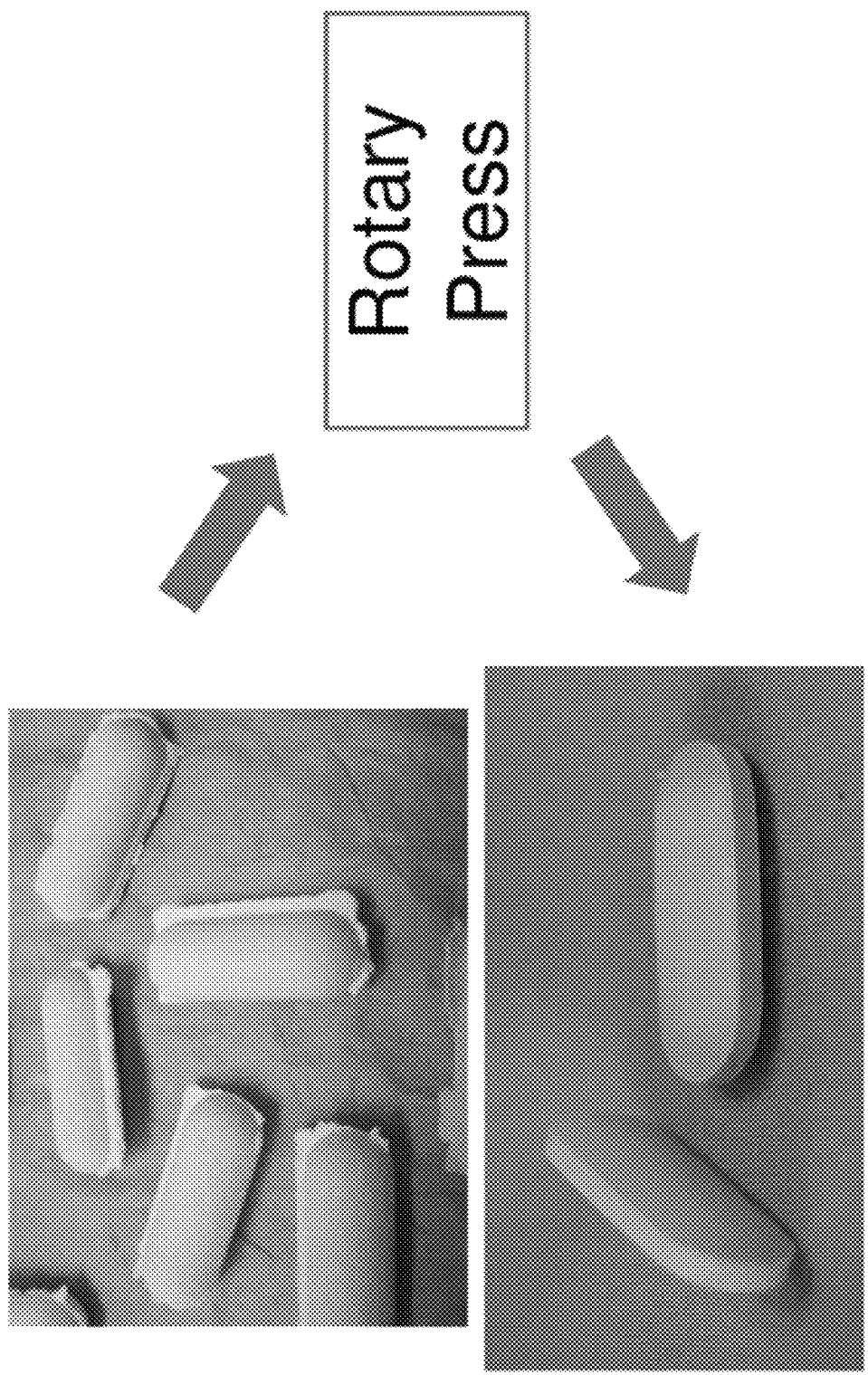

METHOD FOR PRODUCING MONOLITHIC TABLETS

RELATED APPLICATION INFORMATION

This application claims priority to U.S. Application No. 61/410,344 filed on Nov. 4, 2010, the contents of which are herein incorporated by reference in their entirety.

FIELD OF THE INVENTION

The present invention relates to methods for producing monolithic tablets using melt-extrusion technology.

BACKGROUND

Various methods for producing tablets are known in the art. Widely used methods comprise starting materials in powder form, such as the active agent and one or more additive. The starting materials are blended, and the obtained blend is compressed in a die between the moving punches of a tablet press, yielding a tablet. Other methods are based on a sequence of melting and solidification rather than compression. In these methods thermoplastic polymers serve as binders in the final tablet. For the preparation of the tablets, the starting materials, including the thermoplastic binders, the active agents and optionally further additives are blended, heated in an extruder to melt into a homogenous extrudate. The extrudate can be further processed to obtain the desired shape and size of the tablet, for example by directly introducing the extrudate in a cavity of appropriate shape (injection molding). Alternatively, the extrudate can be expelled from the extruder and be shaped using calendars, die cutter, and the like.

A disadvantage of methods requiring the shaping of an extrudate lies in the fact, that the shaping step leaves marks on the finished tablets. After calendering, for example, the tablets may be connected by so-called flash (also referred as burrs) after separation. Even after separating the tablets by additional processes such as cutting the flash, it is difficult to completely remove them. Likewise, tablets formed by injection molding usually also have flash due to the fact that for release of the tablets the injection molding cavity must be opened. For that reason, the wall of the molding cavity is usually formed by two or more partial walls, which form a closed cavity during the shaping step, and are removed to release the shaped tablet. Since it is difficult to create a perfectly smooth surface in the regions, where the partial wall contact each other during the injection molding, extrudate can also enter those regions, leading to flash or at least visible ridges ("burrs") on the surface of the finished tablet. Flash or ridges, however, are aesthetically inacceptable, and might modify the release profile of the active agents, e.g. by altering the surface area or shape of the tablet. In case the tablet is to be swallowed by a higher organism, flash or ridges might even be hazardous by injuring mouth cavities or esophagus or otherwise interfering with swallowing the tablet.

Consequently, the flash (e.g., burrs) have to be removed. Present methods comprise cutting off the flash, or reducing their volume by polishing the surface of the tablets by methods such as tumbling. However, cutting or tumbling may not be effective to completely remove disturbing flash or ridges, but rather leaves remnants thereof, often visible as rough spots, on the surface. Moreover, in the case of tablets made from impact resistant materials, tumbling is ineffective. It is possible to cool down the tablets to temperatures, where the tablet material becomes brittle enough to allow flash removal by tumbling. However, performing the tumbling procedure at low temperature increases the danger of moisture condensation on the surface of the tablets, which may affect the shape of the tablet, cause decomposition of the ingredients or affect the shelf life of the tablet. As such effects are not acceptable, tumbling at low temperatures requires a strict control of ambient moisture, thus rendering the production of the tablets more difficult and more expensive. Therefore, there is a need for a method for obtaining tablets having acceptably even tablet surfaces.

SUMMARY

Surprisingly, in the present invention it was found that the problems mentioned above in the Background section can be avoided and tablets with superior surface characteristics can be produced if an extrudate is compressed between punches of a tabletting press. Specifically, the methods of the present invention allow for the control of the content uniformity of each unit dose of a solid dosage form. Content uniformity is the ability to deliver a dose in a repeatable manner according to the US Pharmacopeia. The methods of the present invention provide flexibility in terms of providing dosage forms with having more conventional shapes that were not previously achievable using melt-extrusion techniques.

In one embodiment, the present invention relates to a method of producing a monolithic tablet. The method comprises the steps of:

a) providing a melt-processed composition containing at least one active agent and at least one thermoplastic binder;

b) charging a predetermined amount by weight of the melt-processed mixture into a die cavity;

c) compressing the melt-processed composition to simultaneously shape and deflash the composition to form a monolithic tablet, using compression equipment; and d) ejecting the monolithic tablet from the die.

Suitably, the die cavity is located between punches within a tabletting press.

In one aspect, the melt-processed composition is rendered plastically deformable by heating prior to compression. In another aspect, the melt-processed composition does not need to be re-heated prior to compression.

The melt-processed composition may comprise plastifying a composition containing at least one active agent and at least one thermoplastic binder by heating and/or shearing to obtain a melt, and forcing the melt through at least one orifice.

Suitably, the melt-processed composition is manufactured by melt-extrusion or injection molding.

In one aspect, particles of the melt-processed composition are fed gravimetrically or by pressure into the die cavity.

Providing particles of the melt-processed composition may comprise calendered pre-shaped lentils, hot spheronization, cold pelletization, or cryo-milling.

In another aspect, pre-shaped bodies of the melt-processed composition are provided, each having a predetermined weight, and a pre-determined number of the pre-shaped bodies is charged into the die cavity.

In yet another aspect, the number of pre-shaped bodies to be charged into the die cavity is one.

In still another aspect, providing pre-shaped bodies of the melt-processed mixture comprises a calendering process.

Providing pre-shaped bodies of the melt-processed mixture may comprise a calendering process to obtain a belt of pre-shaped bodies, the pre-shaped bodies being interconnected by flash; followed by cutting of the belt into individual pre-shaped bodies or strips of pre-shaped bodies prior to feeding the pre-shaped bodies into the die cavity.

In an embodiment, a belt of pre-shaped bodies of the melt-processed mixture is provided, each of the pre-shaped bodies having a predetermined weight, the pre-shaped bodies being interconnected by flash, a pre-shaped body is cut out from the belt and is charged into the die cavity.

The cutting and charging action may be synchronized with the advancing action of the compression equipment or with the advancing of the extruded belt.

In another aspect, the cutting and calendaring is synchronized with the advancing action of the compression equipment or by the advancing of the extruded belt.

Providing the belt of pre-shaped bodies of the melt-processed composition may comprise a calendering process.

In still yet another aspect, the belt of pre-shaped bodies of the melt-processed composition is unwound from a spool.

The belt may comprise a single row of pre-shaped bodies of the melt-processed composition, or the belt may comprise more than one row of pre-shaped bodies of the melt-processed composition. The belt may be cut into a plurality of single-row belts.

In yet another aspect, the melt-processed composition is reheated to a temperature at or above the softening temperature of the composition.

In still yet another aspect, the die cavity or a feed system is provided with temperature control means.

In yet another aspect, at least one punch has an embossed or debossed die face.

In a second embodiment, there is provided a method for producing monolithic tablets. The method comprises the steps of:

a) providing a belt of pre-shaped bodies of a melt-processed composition, the pre-shaped bodies in said belt being interconnected by flash, each pre-shaped body having an predetermined weight, b) cutting the interconnecting flash to obtain singulated or singular pre-shaped bodies, and c) compressing the singulated pre-shaped bodies to simultaneously shape and deflash to obtain monolithic tablets.

In the above method, the cutting and deflashing are performed sequentially. For example, the deflashing can be performed by placing the singular pre-shaped body into a compress to simultaneously shape and deflash the body. Alternatively, in the above method, the cutting and deflashing are performed simultaneously.

In the above method, the cutting and deflashing are performed using a means selected among mechanical means, a laser beam or a water jet. Alternatively, in the above method, the cutting and deflashing are performed using a rotary cutting tool.

In the above method, the cutting and de-flashing are performed using an automated system directly on a cooling belt post calendering and while a production line is running In the above method, the cutting and de-flashing are performed using tumbling below the hardening point of the melt-processed composition.

In the above method, the cutting and de-flashing are performed by blast cleaning. More specifically, the blast cleaning is carried out using a stream of pharmaceutically acceptable particles.

In the above method, the separation and de-flashing are performed by tumbling at a temperature below the hardening point of the melt-processed composition.

In the above method, the separation and de-flashing are performed by tumbling under ultrasound.

In the above method, the separation and de-flashing are performed by a brief exposure to steam, water or a suitable solvent.

The pre-shaped bodies used in the methods of the present invention can be in the form of a cylinder with hemispherical extremities.

BRIEF DESCRIPTION OF THE FIGURES

FIG. 2 is a general schematic outlining the method of the present invention. Starting with the first box of the figure, a blend of ingredients which includes one or more active ingredients and at least one thermoplastic binder (PEO) is provided and then charged in to a melt-extruder to provide an extrudate. The melt-processed composition is then cut to a predetermined weight. The cut melt-processed composition can then optionally heated. If not heated, the extrudate is then compressed in compression equipment. As a result of the compression, the melt-processed composition is shaped and deflashed into a monolithic composition. The monolithic composition can be optionally coated.

FIG. 3 shows the simultaneous shaping and deburring that occur during the compression of the melt-processed composition to form the monolithic tablet according to the methods of the present invention.

DETAILED DESCRIPTION OF THE INVENTION

I. Definitions

Figure 1:
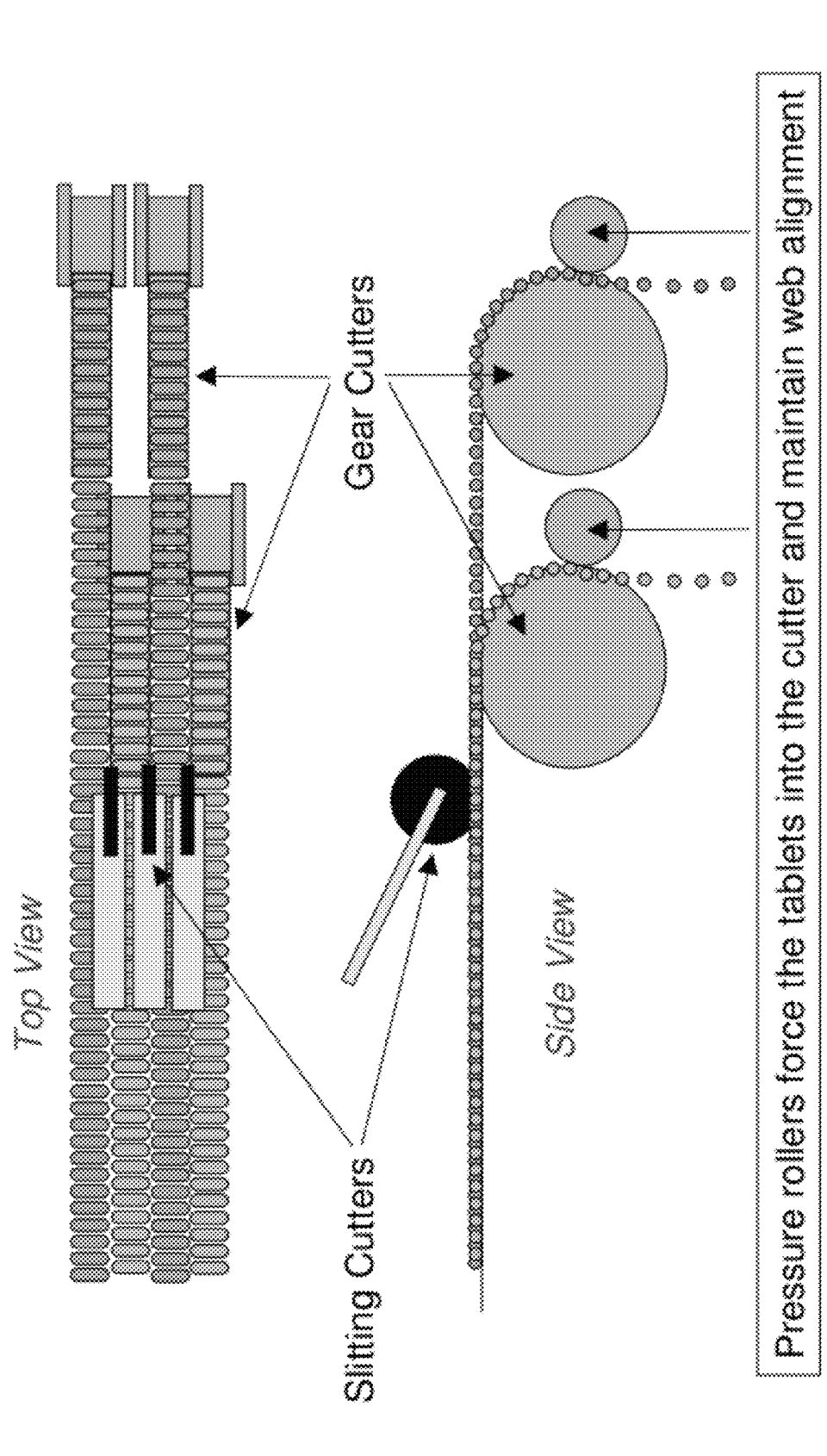
FIG. 1 shows a two step cutting process that can be used pursuant to the methods of the present invention. More specifically, as shown in the figure, slitting cutters can be used to cut pre-shaped bodies from the belt and gear cutters can be used to deflash the pre-shaped bodies. The slitting cutters and gear cutters can be used in series and can be used in a manual method or as part of a continuous production line.

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such dosages are thus encompassed by the scope of the claims reciting the terms "about" and "approximately."

The term "active agent" as used herein refers to one or more chemical entities (or pharmaceutically acceptable salts thereof) that display certain pharmacological effects in a subject and are administered for such purpose. The term "active agent", "active ingredient" and "drug" are used interchangeably herein. The form of the active agent used in preparing the dosage forms of the present disclosure is not critical. For example, active agent used in the method of the present invention can be amorphous or crystalline. The crystalline nature of the active agent can be detected using powder X-ray diffraction analysis, by differential scanning calorimetry or any other techniques known in the art. Examples of active agents that can be used in the present invention are:

Examples of active agents that can be used in the present invention include:

Analgesics, such as, Opioids, Natural opium alkaloids, semi-synthetic opium alkaloids, Morphine, Opium, Hydromorphone, Nicomorphine, Oxycodone, Dihydrocodeine, Diamorphine, Papavereturn, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide, Allylprodine, Prodine, Alphaprodine, Betaprodine, Anileridine, Benzylmorphine, Bezitramide, Buprenorphine, Clonitazene, Diampromide, Dihydromorphine, Dimenoxadol, Dimepheptanol, Dimethylthiambutene, Dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, oxymorphone, papvreturn, paladone, pentazocine, phenadoxone, phenazocine, phenomorphan, phenoperidine, piminodine, propiram, propoxyphene, sufentanil, tapenadol, tilidine, and tramadol;

Anesthetics, such as, for example; Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anesthetics, Fentanyl, Alfentanil, Sufentanil, Phenoperidine, Anileridine, Remifentanil, Other general anesthetics, properidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Other local anesthetics, Ethyl chloride, Dyclonine, Phenol, Capsaicin;

Antiepileptic drug substances such as, for example; Barbiturates and derivatives, Methylphenobarbital, Phenobarbital, Primidone, Barbexaclone, Metharbital, Hydantoin derivatives, Ethotoin, Phenyloin, Amino(diphenylhydantoin) valeric acid, Mephenyloin, Fosphenyloin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide;

Antipsychotic drug substances, such as, for example; Phenothiazines with an aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, properidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone;

Hypnotic and sedative drug substances, such as, for example; Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol;

Anxiolytic drug substances, such as, for example; Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocamil, Etifoxine. Antidepressant drug substances, such as, for example tricyclic antidepressants, non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amphetamine, Dexamphetamine, Metamphetamine, Methylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linpirdine, Nizofenone, Aniracetam, Acetylcarnitine, Idebenone, Prolintane, Pipradrol, Pramiracetam, Adrafinil, Vinpocetine;

Drug substances used in addictive disorders, such as, for example; Nicotine, Bupropion, Varenicline, Disulfuram, Calcium carbimide, Acamprosate, Naltrexone, Buprenorphine, Methadone, Levacetylmethadol, Lofexidine. Antivertigo drug substances, such as, for example; Betahistine, Cinnarizine, Flunarizine, Acetylleucine, other nervous system drugs, Gangliosides and ganglioside derivatives, Tirilazad, Riluzole, Xaliproden, Hydroxybutyric acid, Amifampridine; further drugs such as Ethylmorphine, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, propropizine, Cloperastine, Meprotixol, Piperidione, Tipepidine, Morclofone, Nepinalone, Levodropropizine, Dimethoxanate; opioid agonists/antagonists such as Cyclazonine; opiate analogues such as Desomorphine;

Antiinflammatory and antirheumatic drug substances, such as, for example; Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulphate, Proquazone, Orgotein, Nimesulide, Feprazone, Diacerein, Morniflumate, Tenidap, Oxaceprol, Chondroitin sulphate, Feprazone, Dipyrocetyl, Acetylsalicylic acid, Quinolines, Oxycinchophen, Gold preparations, Sodium aurothiomalate, Sodium aurotiosulphate, Auranofin, Aurothioglucose, Aurotioprol, Penicilamine, Bucillamine;

Antimigraine drug substances, such as, for example; Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, Oxetorone;

Anticholinergic drug substances, such as, for example; Tertiary amines, Trihexyphenidyl, Biperiden, Metixene, Procyclidine, Profenamine, Dexetimide, Phenglutarimide, Mazaticol, Bomaprine, Tropatepine, Ethers chemically close to antihistamines, Etanautine, Orphenadrine (chloride), Ethers of tropine or tropine derivatives, Benzatropine, Etybenzatropine;

Dopaminergic ative substances, such as, for example; Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, other dopaminergic agents, Tolcapone, Entacapone, Budipine;

Anti-dementia drug substances, such as, for example; Anticholinesterases, Tacrine, Donepezil, Rivastigmine, Galantamine, Other anti-dementia drugs, Memantine, *Ginkgo biloba*; and other nervous system drug substances, such as, for example; Parasympathomimetics, Anticholinesterases, Neostigmine, Pyridostigmine, Distigmine, Ambenonium, Choline esters, Carbachol, Bethanechol, Other parasympathomimetics, Pilocarpine, Choline alfoscerate.

Examples of other active agents include antibiotics, analgesics, vaccines, anti-diabetic agents, antifungal agents, antineoplastic agents, anti-parkinsonian agents, anti-viral agents (such as, for example, amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista)), appetite suppressants, biological response modifiers, cardiovascular agents, central nervous system stimulants, chemotherapeutic agents (such as, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, a Bcl-x1 inhibitor, an HDAC inhibitor, a c-MET inhibitor, a PARP inhibitor (such as, for example, PJ34, AG14699, AG14361, CEP-6800, CEP-8983, INO-1001, KU59436, BSI-201, GPI 21016, GPI15427 or AZD2281), a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-1-TM-601, ALT-110, BIO 140, CC 8490, cilengitide, gimatecan, IL13-PE38QQR, INO 1001, IPdR, KRX-0402, lucanthone, LY 317615, neuradiab, vitespan, Rta 744, Sdx 102, talampanel, atrasentan, Xr 311, romidepsin, ADS-100380, chlamydocin, JNJ-16241199, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]-benzoyl]-, disodium salt, heptahydrate, camptothecin, irinotecan; PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyclophosphamide, cyproterone, cytarabine, dacarbazine, dactinomycin, daunorubicin, diethylstilbestrol, epirubicin, fludarabine, fludrocortisone, fluoxymesterone, flutamide, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa), contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, respiratory agents, skin and mucous membrane agents, smoking cessation agents, steroids, urinary tract agents, uterine relaxants, vaginal agents, vasodilator, anti-hypertensive, hyperthyroids, anti-hyperthyroids, anti-asthmatics and vertigo agents.

As used herein, the term "cutting" refers to any process which is suitable of separating one entity into two entities. For example, cutting can involve separating two pre-shaped bodies interconnected by a flash into two singulated or singular pre-shaped bodies (thus forming two individual pre-shaped bodies) by dividing or removing the interconnecting flash. Cutting can include the use of a blade or blade-like device.

As used herein, the term "glass transition temperature" or "$T_g$" refers to temperature at which an amorphous solid becomes soft upon heating or brittle upon cooling. More specifically, as the temperature of a polymer drops below $T_g$, it behaves in an increasingly brittle manner. As the temperature rises above the $T_g$, the polymer becomes more rubberlike. In general, values of $T_g$ well below room temperature define the domain of elastomers and values above room temperature define rigid, structural polymers.

As used herein, the term, "monolithic" when used in connection with the term "tablet" refers to a tablet comprised of one continuous block of solid having at least one dimension that is more than 5 millimeters. In contrast to "monolithic tablets", "multiparticulate" tablets, are comprised of a plurality of discrete subunits. These subunits are separated, e.g., by grain boundaries. Such tablets, although seemingly constituting one block of solid, usually disintegrate in the stomach or in the intestines, thereby simultaneously or successively releasing the individual subunits. Alternatively for an eroding matrix, materials are released at predetermined rates.

By "pharmaceutically acceptable," refers in a broad sense to compounds, materials, compositions and/or dosage forms, which are, within the scope of sound medical judgment, suitable for use in contact with tissues of a subject without excessive toxicity, irritation, allergic response, or other problems or complications, commensurate with a reasonable benefit/risk ratio.

As used herein, the term "softening temperature" refers to a temperature (or a temperature range) above the glass transition temperature or the melting point of semicrystalline domain, where a material becomes thermoplastic.

The term "subject" refers to an animal. In one aspect, the animal is a mammal, including a human or non-human. The terms patient and subject may be used interchangeably herein.

As used herein, the term, "thermoplastic" when describing a binder or polymer refers to one or more materials that melt and/or soften when heat is applied to allow molding while maintaining good chemical stability. Exemplary pharmaceutically acceptable thermoplastic polymers that may be used in the present invention include (1) homopolymers and copolymers of N-vinyl lactams, especially homopolymers and copolymers of N-vinyl pyrrolidone, e.g. polyvinylpyrrolidone (PVP), copolymers of N-vinyl pyrrolidone and vinyl acetate or vinyl propionate; (2) cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate; (3) high molecular polyalkylene oxides such as polyethylene oxide and polypropylene oxide and copolymers of ethylene oxide and propylene oxide, (4) polyvinyl alcohol-polyethylene glycol-graft copolymers (available as Kollicoat® IR from BASF AG, Ludwigshafen, Germany); (5) polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates); (6) polyacrylamides; (7) vinyl acetate polymers such as copolymers of vinyl acetate and crotonic acid, partially hydrolyzed polyvinyl acetate (also referred to as partially saponified "polyvinyl alcohol"); (8) polyvinyl alcohol; (9) oligo- and polysaccharides such as carrageenans, galactomannans and xanthan gum, or mixtures of one or more thereof. In one aspect of the present invention, the thermoplastic binder is a pharmaceutically acceptable polymer, such as poly(ethylene oxide).

II. Methods for Producing Monolithic Tablets

A. Use of Compression with Individually Separate Calendered Intermediates

In one embodiment, the present invention relates to a method for producing a monolithic tablet. The method comprises the steps of:

a) providing a melt-processed composition comprising a mixture of at least one active agent and at least one thermoplastic binder;

b) charging or introducing a predetermined amount by weight of the melt-processed composition into a die cavity;

c) compressing the melt-processed composition to shape and deflash the composition into a monolithic tablet, using compression equipment; and d) ejecting the monolithic tablet having the final tablet shape from the die.

In step a) of the method of the present invention, a melt-processed composition containing a mixture of at least one active agent and at least one thermoplastic binder is provided. Methods and techniques for making such a melt-processed composition, such as by melt-extrusion or injection molding, are well-known to those skilled in the art. For example, such a melt-processed composition comprising the mixture of the at least one active agent and the at least one thermoplastic agent can be prepared by mixing the at least one active agent(s) and the at least one thermoplastic binder(s) to form a mixture. The mixture is heated until melted and then homogenized to provide a uniform melt. This uniform melt is then cooled. The process of providing a melt-processed composition can comprise plastifying a composition containing the at least one active agent and the at least one thermoplastic binder by heating and/or shearing to obtain a melt, and then forcing the melt through at least one orifice.

As mentioned previously herein, techniques for melt-extrusion and injection molding techniques are well known to those skilled in the art. Specifically, melt-extrusion involves mixing or kneading the heated mixture in an extruder. Suitable extruders for heating and kneading the heated blend include single screw extruders, intermeshing screw extruders or multiscrew extruders (such as twin screw extruders), which can be corotating or counterrotating. The extruders can be optionally equipped with kneading disks or other screw elements for mixing or dispersing the melt.

It will be appreciated by those skilled in the art that the working temperatures of melt-extrusion or injection molding will be determined, in part, by the properties of the active agent (including, for example, the melting point of the active agent) and the thermoplastic binder(s) as well as by any pharmaceutically acceptable excipients (such as, for example, one or more fillers, binders, lubricants/glidants, solubility enhancing agents, suspending agents, sweetness and/or flavoring agents, preservatives, buffers, wetting agents, disintegrating agents, effervescent agents, surfactants, humectants, solution retarders, absorbents, solvents, other pharmaceutically acceptable additives and combinations thereof) which might be optionally present, as well as by the kind of extruder or the kind of configuration within the extruder that is being used. A portion of the energy needed to melt the mixture in the extruder can be provided by heating elements. However, the friction and shearing of the material in the extruder can also provide a substantial amount of energy to the mixture and aid in the formation of a homogeneous melt of the components. After leaving the extruder through an orifice, the melt-processed composition is considered to be an "extrudate", which can be subject to further processing. For example, the melt-process composition or extrudate can be cut into various size pieces (which can be referred to herein as individual tablet intermediates) of any size and/or weight. In fact, the extrudate can be cut to a specific size in order to provide a piece of extrudate having a desired predetermined weight.

In step b) of the method, a predetermined amount by weight of the melt-processed composition or extrudate (said predetermined amount by weight of the melt-processed composition or extrudate being referred to herein as an individual tablet intermediate) is charged, introduced, inserted or placed into a die cavity. The contours of the die cavity match the desired form of the tablet.

The predetermined amount by weight of the melt-processed composition or extrudate (e.g., individual tablet intermediate) equals or is within limits acceptable in the art of tablet manufacturing and can be readily determined by one skilled in the art. Specifically, the predetermined amount by weight of the melt-process composition or extrudate (e.g., individual tablet intermediate) is close or equal to the intended final weight of the monolithic tablet having its final tablet shape.

In one aspect of the method of the present invention, pre-shaped bodies of the melt-processed composition or extrudate (namely, the individual tablet intermediates) are provided. Each pre-shaped body has a predetermined weight. A pre-determined number of the pre-shaped bodies are then charged, introduced, inserted or placed into the die cavity. The number of pre-shaped bodies to be inserted or filled into the die cavity can be any number from one up to 1000, such as, for example, 1 to 100, 1 to 50, 1 to 25, 1 to 10, 1 to 7, 1 to 5, such as 1, 2, 3, 4 or 5 pre-shaped bodies. Ultimately, however, there is no limit to the number of pre-shaped bodies that can be fed continuously into the die cavity. Each particle may constitute a considerably fraction of the predetermined weight, e.g. 100 percent, 50 percent or 25 percent of said weight. In another aspect of the present invention, the number of pre-shaped bodies to be filled into the die cavity is one. In this case, the predetermined weight matches, within limits that are acceptable in the art of tablet manufacturing, the intended final weight of the tablet.

The shape of the bodies is not critical and may be selected from a variety of shapes. If one pre-shaped body is charged into the die cavity, it may have a shape, which is already close to the shape of the final tablet. However, any other shape is acceptable, as long as its dimensions do not impede charging, introducing, inserting or placing the pre-shaped body into the die cavity. Examples of such shapes include spheres, elongated spheres, such as e.g. ellipsoids or asymmetrical ellipsoids having an egg-like shape, spheres with hemispherical extremities, cylinders with hemispherical extremities, cylinders with round or polygonal cross section, such as pentagonal, hexagonal, heptagonal or octagonal cross section, cubes, elongated cubes, pyramids, and the like.

In one aspect of the invention, the pre-shaped bodies (individual tablet intermediates) are obtained by a calendering process. Calendering is a process well-known in the art for shaping thermoplastic materials. In a calender, gaps are formed by one or more sets of counterrotating rolls, or by rolls arranged over a transport belt. The thermoplastic material can be a hot extrudate (a melt-processed composition) that has just left the extruder and has a temperature that still ensures thermoplasticity. If appropriate, the extruder temperature can be lowered to temperatures suitable for calendering using suitable cooling means. Examples for suitable cooling means include cooling chambers through which the extrudate or the thermoplastic material passes before entering the calender, or refrigerated transport bands. As the thermoplastic material is forced through one or more gaps between such sets of rolls or between rolls and the transport band, the structures on the surface of the gap(s) and/or the moving transport belt are imprinted on the thermoplastic material, thus determining or imparting the shape on the thermoplastic material. By appropriate arrangements of elevations and depression on the surface of the counterrotating rolls, or on the surface of a roll and, where applicable, on the transport belt forming a gap together with the roll, calendering can transform the thermoplastic material into pre-shaped bodies. The pre-shaped bodies may be a precursor to the final tablet shape so as to minimize the extent of plastic deformation and/or facilite transport through the feeding system of the press. The pre-shaped bodies may take a variety of forms, such as, spheres, elongated spheres, such as e.g. ellipsoids or asymmetrical ellipsoids having an egg-like shape, cylinders with round or polygonal cross section, such as pentagonal, hexagonal, heptagonal or octagonal cross section, cubes, elongated cubes, pyramids, and the like. In particular, the pre-shaped bodies may take a form reminiscent of a tablet, e.g. a coin-like form (flat cylinder) or a lentil-like form. If the elevations and depressions on the surfaces of the rolls or the transport belt are arranged such that between two combinations thereof, each of which forming a pre-shaped body, a thin strand of thermoplastic material can pass through the gap, a belt of pre-shaped bodies will be formed, wherein the pre-shaped bodies will be connected by so-called flash, i.e. thin bridges of thermoplastic material between the pre-shaped bodies. If the elevations on the rolls and/or the transport belt repeatedly touch during the revolution of the rolls, the calender squeezes off the strand of extrudate or thermoplastic material at those spots, thus discharging unconnected pre-shaped bodies.

In step c) of the method of the present invention, the melt-processed composition is compressed and shaped into a monolithic tablet. Compression equipment (such as tablet presses (such as single-punch machines, rotary tablet machines, high-speed rotary tablet machines, multilayer rotary tablet machines, etc.), a roller compactor, etc.) is used for compressing and shaping. Such compression equipment and its use thereof is well known to those skilled in the art. In compression, a force is used which presses the melt-processed composition against the die thereby having the effect that the composition adopts the shape stipulated by the die surface at the moment of compression. The melt-processed composition is, at least to some degree, plastically deformable at the temperature prevailing during the compression. In step c), in one aspect, the shaping and deflashing occur simultaneously.

If the predetermined amount by weight of the melt-processed composition or extrudate (individual tablet intermediate) is constituted by a multitude of the particles of the melt-processed composition, each of which only represent a small fraction of the predetermined amount by weight, the compression unites the particles into on monolithic tablet, which matches the shape of the die cavity. In the event that the shape of the melt-processed composition already matches or is identical the intended final shape of the tablet, except for surface defects such as flash (burrs), rims, rough spots, blebs or the like, pressing against the surface of the die removes said defects.

In step d), the monolithic tablet is ejected from the die, using means well-known in the art, such as deflectors.

The die cavity is suitably located between punches of a tablelting press. The punches may, e.g. be opposed movable punches. For example, a lower punch seals off the bottom of the die cavity, which then is charged with the predetermined amount of the melt-processed composition or extrudate. An upper punch is lowered and seals off the top of the die cavity. By pressing the upper punch against the lower punch, the predetermined amount of melt-processed composition or extrudate, are compressed into a monolithic tablet. The upper punch is then retracted from the die cavity, the lower punch is pushed upwards and thereby ejects the monolithic tablet from the die cavity.

If the melt-processed composition or extrudate does not have sufficient plastic deformabilty at ambient temperature, the melt-processed composition or extrudate may be rendered plastically deformable by heating prior to compression, for example by heating or re-heating prior to charging into the die cavity. This heating may occur outside of the compression equipment. For example, the melt-processed composition or extrudate may be placed into an oven or may pass through a heating zone before being transferred into the compression device. Alternatively, the die cavity or a feed system, which is used to introduce the melt-processed composition or extrudate into the compression equipment, can be equipped with temperature control means. Said temperature control means allow actively changing the temperature of the melt-processed composition, in particular heating it from a lower temperature to the desired temperature (by heating elements). Optionally, the heating means may also comprise measuring probe for determining the temperature of the melt-processed composition.

Typically, the calendaring process yields a belt of pre-shaped bodies, wherein the pre-shaped bodies are interconnected by flash. Belts of pre-shaped bodies to be used in a method according to the invention in general may comprise a single row of pre-shaped bodies, which are interconnected by flash, or may comprise more than one row of pre-shaped bodies. A belt comprising more than one row represents a matrix of pre-shaped bodies, wherein pre-shaped bodies of one row are interconnected by flash, and wherein pre-shaped bodies of neighboring rows also are interconnected by flash. The thickness of the flash between pre-shaped bodies of one row may be identical to or different from the thickness of the flash between pre-shaped bodies of neighbouring rows. A belt representing a single row may comprise 2 to 10, or more than 10, such as tens, or hundreds, or thousands, or tens of thousands, or hundreds of thousands of pre-shaped bodies. For example, a belt may comprise a number of pre-shaped bodies in the range from 10 to 100,000, 100 to 10,000, or 1,000 to 5,000. In belts comprising more than one row, the number of rows may, e.g., range from 2 to 1,000, 2 to 100, 2 to 50, 2 to 25, or 2 to 10. Preferred belts comprising more than one row comprise 5 to 15, 6 to 14, 7 to 13, 8 to 12, or 9 to 11 rows. In particular, a belt may comprise 7, 8, 9, 10, 11 or 12 rows. The length of each individual row may be as described for belts comprising one row.

In one aspect, the belt of the pre-shaped bodies is cut or separated into either individual pre-shaped bodies or into strips of pre-shaped bodies, wherein cutting may be performed by technologies known in the art, such as by the action of knives, cutting blades etc. Strips of pre-shaped bodies may either be shorter portions of a single row, or smaller portions of a matrix (thus comprising shorter portions of two or more neighboring rows). For example, a belt comprising one row of 2000 pre-shaped bodies may be separated into 2000 individual pre-shaped bodies, or into 20 rows, each of which comprising 100 pre-shaped bodies interconnected by flashed, or into 40 rows, each of which comprising 50 pre-shaped bodies. A belt comprising 10 rows, each of which comprising 1,000 pre-shaped bodies, may for example be cut into 10,000 individual pre-shaped bodies, or into 10 rows, each of which comprising 1,000 pre-shaped bodies, or into two matrices, each of which comprising 5 rows with 1,000 pre-shaped bodies and a total number of 5,000 pre-shaped bodies per matrix, or into 1000 small matrices, each of which comprising 2 rows of 5 pre-shaped bodies. Finally, the individual bodies, the rows of pre-shaped bodies, or the smaller matrices of pre-shaped bodies as obtained by cutting, are fed into the die cavity. In a continuous process, the number of pre-shaped bodies per row could be unlimited. The pre-shaped bodies that are obtained by cutting are collected via a suitable feeding and then sent to compression equipment for shaping and deflashing.

The cutting and charging action may be synchronized with the advancing action of the compression equipment. Consequently, the overall production process can be synchronized in an advantageous manner, obviating the necessity to coordinate two separate subprocesses (i.e. cutting the belt of pre-shaped bodies and charging the cut belt into the die cavity), but efficiently combines both subprocesses into one integrated process. For example, a pre-shaped body can be stamped out from the belt by the upper edge of the die wall and the upper punch by the advancing action of the upper punch, and the pre-shaped body is simultaneously charged into the die cavity.

Additionally, the cutting and calendaring action may be synchronized with the advancing action of the compression equipment.

A belt of pre-shaped bodies to be used in a method according to the invention may be unwound from a spool. This option is applicable for all melt-processed compositions which, at the temperature of the belt during unwinding are not brittle, but has enough flexibility to be unwound. The present invention therefore also comprises a method for storing belts of pre-shaped bodies by winding up said belts on spools. The process of winding up may be performed after producing the belt, e.g. by calendering, optionally after cooling down the belts to temperatures where the tensile strength in particular of the interconnecting flashed is high enough to prevent tearing of the belt during winding up. In the present invention, the belts of pre-shaped bodies on the spools constitute a useful storage form, which allows storing the belts in a form which is compact; which easily can be protected from environmental conditions such as radiation, dust, chemical or microbial contamination by sealing in suitable containers, such as plastic bags, metal or glass containers; and which easily can be reactivated for use in a method for producing a monolithic tablet according to the invention. Said reactivation may comprise inserting the spool in a device for unwinding the belt of pre-shaped tablets for subsequent cutting into individual pre-shaped bodies, or strips (having a single row of pre-shaped bodies) or matrices (having more than one row) of pre-shaped bodies, and/or for subsequent feeding of the belt, the strips, the matrices or the individual pre-shaped bodies into a die cavity for producing a monolithic tablet. Alternative methods for storing belts comprise curling up the belts of pre-shaped bodies in the absence of a spool, or folding up the belts. Inadvertent uncurling or unfolding of the belts may be prevented by fastening means, such as ribbons, wrappings or boxes, which contain the curled up or folded belts. From such storage forms, the belts may be uncurled or unfolded. In particular, boxes containing curled or folded belts may serve as dispenser devices from which one end of the belt can be inserted into a device for uncurling or unfolding the belt, cutting and/or charging the belt into die cavities.

In all aspects of the methods for producing a monolithic tablet as described in this section, the melt-processed composition may be transferred from melt processing via optional steps, such as providing particles or providing pre-shaped bodies or cutting belts of pre-shaped bodies, into the die cavity without additional heating steps. For example, a melt-processed composition can be extruded in a thermoplastic state, immediately or after moderate cooling be shaped into pre-shaped bodies or belts of pre-shaped bodies by calendering in a still thermoplastic state, and, optionally after cutting into shorter belts or individual pre-shaped bodies, be charged into a die cavity for compression and shaping into a monolithic tablet.

Alternatively, all embodiments of methods for producing a monolithic tablet as described in this section may also comprise reheating the melt-processed composition to a temperature at or above the softening temperature of the composition. During the compression step c) of the method according to the invention, the temperature of the melt-processed composition or extrudate can be at or above the softening point of the respective melt-processed composition or extrudate to allow a shaping into the desired shape. Alternatively, in the case of melt-processed compositions or extrudate already having the desired shape, but displaying defects, such as minor deviations from the intended form, or remnants of interconnecting flash on individual pre-shaped bodies after cutting belts of interconnected pre-shaped bodies, a temperature at or above the softening point allows correcting such defects or incorporating the flash remnants into the pre-shaped body, yielding an acceptable surface. In one aspect, the interconnecting flash in the belts of pre-shaped bodies can be thin. Wherein the weight of a pre-shaped body in a belt of pre-shaped bodies matches the intended final weight, the weight of interconnecting flashes or cut flashes will not significantly alter the final weight of the tablet. Alternatively, the weight of the flashes can be taken into consideration when setting the weight of the pre-shaped bodies, thus exactly reaching the intended final weight after incorporation the flash remnants into the tablet during compression. Examples for thin flash are flash, the thickness of which corresponds to a range of 0.1% to 25% of the thickness of the pre-shaped body, such as 25%, 20%, 10%, 5%, 3%, 1%, or 0.1% of the thickness of the pre-shaped body, or is selected from a range of 50 micrometers to 1000 micrometers, such as 1000 µm, 500 µm, 250 µm, 200 µm, 150 µm, 125 µm, 100 µm, 75 µm, or 50 µm.

Reheating of the melt-processed composition or extrudate may be required when the subprocesses of providing the melt-processed composition in step a) and compressing the melt-processed composition in step c) are temporally separated enough to allow a decrease of the temperature of the melt-processed composition below the softening point. Reheating is optionally when storage forms as described above are used. Optionally, no reheating is necessary. Reheating can be achieved by various ways, such as continuous passing of the melt-processed composition though a heated zone (in continuous production processes) or transfer of the melt-processed composition into a heated zone, such as an incubator, and removing it from that zone before further processing (discontinuous production process). In particular, reheating can occur immediately prior to charging or introducing the predetermined amount of the melt-processed composition or extrudate into the die cavity, in the compression device itself, such as a tablet press or in a separate device prior to transferring the reheated melt-processed composition into the compression device. In case the method comprises cutting a belt of pre-shaped bodies prior to charging strips of pre-shaped bodies or individual pre-shaped bodies into the die cavity, heating may occur before cutting, but occurs after cutting and before charging into the die cavity.

In all aspects of methods according to the invention, at least one punch optionally has an embossed or debossed die face, or combinations thereof. Said die faces allow modelling the surface of the tablet by creating scores or ridges. Said scores or ridges enlarge the surface of the tablet, thus allowing a modification of the release of the active agents. Alternatively, they can be used to display logos or other information. Scores on tablets may in particular be used to define breaking lines for safe and accurate dividing tablets into subunits. The tablets can also be printed.

The monolithic tablets of the invention can be provided in unit dosage form, for example, in the form of tablets, pills or suppositories, suitable for administration to humans, non-human mammals or other animal. The administration may be oral, by implantation into tissues, e.g. subcutaneous, vaginal or anal. The amounts of active agents(s) will depend on the respective ingredients, the patient group to be treated in dependence of factors such as age, gender, severity of the treated condition, the intended frequency of administration. Such factors are known to those skilled in the art and can be determined appropriately. While therefore exact amounts are determined in each case, examples for generic ranges of amounts of active agent are from 0.01 mg to 5000 mg, from 0.1 mg to 500 mg, or from 1 mg to 50 mg.

The monolithic tablets made pursuant to the processes described herein can be further treated as customary in the art of tablet manufacturing, e.g. they can be provided with a film coat. A film coat can optionally contain part of an active agent or ingredients. Alternatively a film coat can also improve taste and provides an elegant appearance. If desired, the film coat may be an enteric coat. The film coat usually includes a polymeric film-forming material such as hydroxypropyl methylcellulose, hydroxypropyl cellulose, acrylate or methacrylate copolymers or polyvinyl alcohol-polyethylene glycol graft copolymer. Besides a film-forming polymer, the film coat may further comprise a plasticizer, e.g. polyethylene glycol, a surfactant, e.g. a Tween® type, and optionally a pigment, e.g. titanium dioxide or iron oxides or commonly used dyes. The film-coating may also comprise talc as anti-adhesive.

B. Use of Compression with Individually Separate Calendered Intermediates

In a second embodiment, the present invention generally relates to a method for producing monolithic tablets. The method comprises the steps of:

a) providing a belt of pre-shaped bodies of a melt-processed composition, the pre-shaped bodies in said belt being interconnected by flash, each pre-shaped body having an predetermined weight (which can be weight to volume—the weight is controlled by the volume of the molding cavity);

b) cutting the interconnecting flash to obtain singulated pre-shaped bodies, and c) deflashing the singulated pre-shaped bodies to obtain monolithic tablets.

In one aspect of the present invention, after the cutting and deflashing of the pre-shaped bodies, no further shaping of the obtained monolithic tablets is required.

The belts and the pre-shaped bodies contained within said belt that are interconnected by flash can be the belts and pre-shaped bodies as described above in Section A in the context of the method for producing a monolithic tablet. In addition, the belts and the pre-shaped bodies contained within the belt that are interconnected by flash can also be pre-shaped bodies which are not used for producing tablets or for pharmaceutical purposes.

With respect to the cutting and deflashing a belt of pre-shaped bodies of a melt-processed composition, said belt is formed by pre-shaped bodies, which have an predetermined weight and are interconnected by flash. The method of the present invention comprises cutting of the interconnected flash in the belt to obtain individual pre-shaped bodies, and, simultaneously with cutting or sequentially after cutting, comprises the deflashing of the pre-shaped bodies.

In one aspect, the method can comprise cutting only one interconnecting flash, thereby separating one terminal pre-shaped body from the remainder of the belt. Alternatively, the method can comprise cutting the belt into two strips of interconnected pre-shaped bodies. In another aspect, several interconnecting flash are cut, thus releasing a mixture of individual pre-shaped bodies and/or strips of interconnected pre-shaped bodies thereby separating all the interconnecting flash of a belt. In still yet another aspect, all interconnecting flash are cut, thus turning a belt of pre-shaped bodies into individual pre-shaped bodies.

In the method of the present invention, the cutting of step b) and the deflashing of step c) can be performed simultaneously. Alternatively, both steps can be performed sequentially, e.g., namely, step c) of deflashing being performed subsequently after cutting in step b).

In the event that the cutting and deflashing are performed simultaneously, the act of cutting automatically also causes deflashing of the released pre-shaped body or the strip of pre-shaped bodies. In case cutting and deflashing occur sequentially, cutting will release a pre-shaped body (or a strip of pre-shaped bodies) having at least a remnant of the cut interconnecting flash. Said remnant is deflashed after cutting, wherein deflashing may occur using the same means as used for cutting, or may occur using a separate means.

Suitable means that can be used for cutting and/or deflashing may, e.g., be selected from mechanical means (including, robotic mechanical means), such as linear, rotary or scissor-like cutting tools, or tumbling, from a laser beam, and from a fluid jet, such as a water jet. Robotics may, for example, be characterized by one or more features, selected among the ability of movement with one or, in particular, several degrees of freedom, the ability to be programmed and/or controlled by software or a computer, the ability of sending feedbacks to a control software or computer, the ability of having more than one functionality, or the ability of sensing the environment and performing actions in response to the detected environmental situation. However, instead of the previously mentioned characteristics, other characteristics commonly used for defining robotics may apply.

In one aspect, simultaneous or sequential cutting and deflashing are performed using a rotary tool. In the case of simultaneous cutting and deflashing, the rotary tool may, e.g., cut out the interconnecting flash, releasing pre-shaped bodies without remnants of flash. In the case of sequential cutting and deflashing, the rotary tool may, e.g divide the interconnecting flash, releasing pre-shaped bodies having remnants of flash, which in a subsequent step are removed, e.g. by tumbling, by the action of a robotic arm, and the like.

In another aspect, while the belt is on a cooling belt to lower the temperature after calendering, cutting and deflashing are performed directly on the cooling belt by a robot. For example, cutting and deflashing may be performed by a precise cutting functionality integrated in the robot, leaving no remnants of flash, or cutting may be performed by a cutting functionality and subsequent deflashing may be performed by a tumbling functionality integrated in the robotic arm. Cutting and deflashing can be performed while the production line, which comprises calendering and cooling after calendering, is running The production line may, for example, be a production line for producing cut and deflashed pre-shaped bodies, or a production line for producing monolithic tablets, e.g. final tablets as referred to above. The production line may for example be running in a stepwise mode, and in particular may be running in a continuous mode.

In still another aspect, the cutting and deflashing may be performed sequentially or simultaneously using tumbling below the hardening point of the melt-processed composition.

In yet still another aspect, a two step cutting process can be used (See FIG. 1). Slitting cutters can be used to cut the pre-shaped bodies from the belt and gear cutters can be used to deflash the pre-shaped bodies. The use of said slitting cutters and gear cutters can be used in series and can be used in a manual method or as part of a continuous production line.

In still yet another aspect, the separation and deflashing are performed by so-called "blast cleaning" using projectiles. In particular, the projectiles may be particles of a pharmaceutically acceptable excipient or a mixture of such excipients. In one aspect, a pharmaceutically acceptable excipient or a mixture of pharmaceutically acceptable excipients may be used which is already present in the melt-processed composition underlying the pre-shaped bodies.

In still yet another aspect, separation and de-flashing are performed by tumbling at a temperature below the hardening point of the melt-processed composition.

In yet still another aspect, the separation and deflashing are performed by tumbling under ultrasound. While not wishing to be bound by any theory, the thermoplastic binder (polymer) represented by the melt-processed composition behaves in a glassy manner by reducing its loss modulus under dynamic deformations of sufficient frequency. Appropriate frequencies for given melt-processed compositions can routinely be determined by those skilled in the art.

In still yet another aspect, separation and de-flashing are performed by or comprise a brief exposure to steam, water or a suitable solvent. Said exposure softens the flash before softening the pre-shaped bodies. While variations may occur depending on the melt-processed composition used, it is assumed that in general the diffusion time of said agents to the center line of the flash is at least one order of magnitude smaller than the diffusion time necessary to induce superficial swelling of the pre-shaped bodies. Suitable solvents for use on a given melt-processed composition can readily be determined by those skilled in the art.

The melt-processed composition to be used in this process for cutting and deflashing a belt of pre-shaped bodies may be any formulation, but in particular may be a melt-extrudate, such as an extrudate as described in context with the method for producing a monolithic tablet as described above in Section A.

The pre-shaped bodies to be subjected to the method for producing a monolithic tablet may—after performing the method on them—be used for their intended purpose, for example a use as tablets (and may for example constitute the final tablets as referred to in the context of the method for producing a monolithic tablet according to the first aspect of the invention), or may be subjected to further processing steps, such as for example coating and/or packaging.

What is claimed is:

1. A method for producing monolithic tablets, the method comprising the steps of:
    a) providing a belt of pre-shaped bodies of a melt-processed composition, the pre-shaped bodies in said belt being interconnected by flash, each pre-shaped body having an predetermined weight;
    b) cutting the interconnecting flash in the belt to obtain singulated pre-shaped bodies;
    c) charging the singulated pre-shaped bodies into a die cavity; and
    d) compressing the singulated pre-shaped bodies to simultaneously shape and deflash to obtain monolithic tablets, wherein the pre-shaped bodies adopt the shape of the die surface upon compressing.

2. The method of claim 1, wherein cutting and deflashing are performed sequentially.

3. The method of claim 1, wherein cutting and deflashing are performed simultaneously.

4. The method of claim 1 wherein the pre-shaped bodies are a cylinder with hemispherical extremities.

* * * * *